United States Patent [19]

Schweizer et al.

[11] 3,932,038

[45] Jan. 13, 1976

[54] APPARATUS FOR THE CONTINUOUS MEASUREMENT OF THE DENSITY OF A LIQUID BY UTILIZATION OF THE LAW OF REFRACTION

[75] Inventors: Walter Schweizer, Berlin; Martin-Ulrich Reissland, Gummersbach, both of Germany

[73] Assignee: VDO Adolf Schindling AG, Frankfurt am Main, Germany

[22] Filed: July 2, 1974

[21] Appl. No.: 485,226

[30] Foreign Application Priority Data
July 4, 1973   Germany............................ 2333945

[52] U.S. Cl. ................ 356/133; 250/573; 356/135
[51] Int. Cl.² ........................................ G01N 21/46
[58] Field of Search ............ 250/573; 356/128, 133, 356/134, 135

[56]   References Cited
   UNITED STATES PATENTS

| | | | |
|---|---|---|---|
| 2,569,127 | 9/1951 | Eltenton ............................ | 356/133 |
| 2,972,926 | 2/1961 | Goldberg et al. .................. | 356/135 |
| 3,282,149 | 11/1966 | Shaw et al. ...................... | 356/133 |
| 3,362,224 | 1/1968 | Melone .............................. | 356/133 |
| 3,426,211 | 2/1969 | Anderson .......................... | 356/135 |
| 3,520,619 | 7/1970 | Ward ................................. | 356/133 |

*Primary Examiner*—Alfred E. Smith
*Assistant Examiner*—Richard A. Rosenberger
*Attorney, Agent, or Firm*—Otto John Munz

[57]   ABSTRACT

An apparatus for continuous measurement of the density of a liquid within prespecified limits, by utilization of the law of refraction, particularly for the continuous measurement of acid density of a storage battery of a motor vehicle for the purpose of determining the state of charge of the battery.

The apparatus is equipped with a photoconductive rod, a light source which radiates a pencil of parallel or nearly parallel rays into the rod toward a measuring surface, located at the end of the rod immersed in the liquid. The surface is struck by the pencil of rays at an angle with respect to the surface that equals at most the total reflection angle occurring at the lower limit of liquid density. A photosensitive element is located in the path of the ray pencil opposite a surface deflecting the pencil of rays, which is refracted by the measuring surface into the liquid.

9 Claims, 1 Drawing Figure

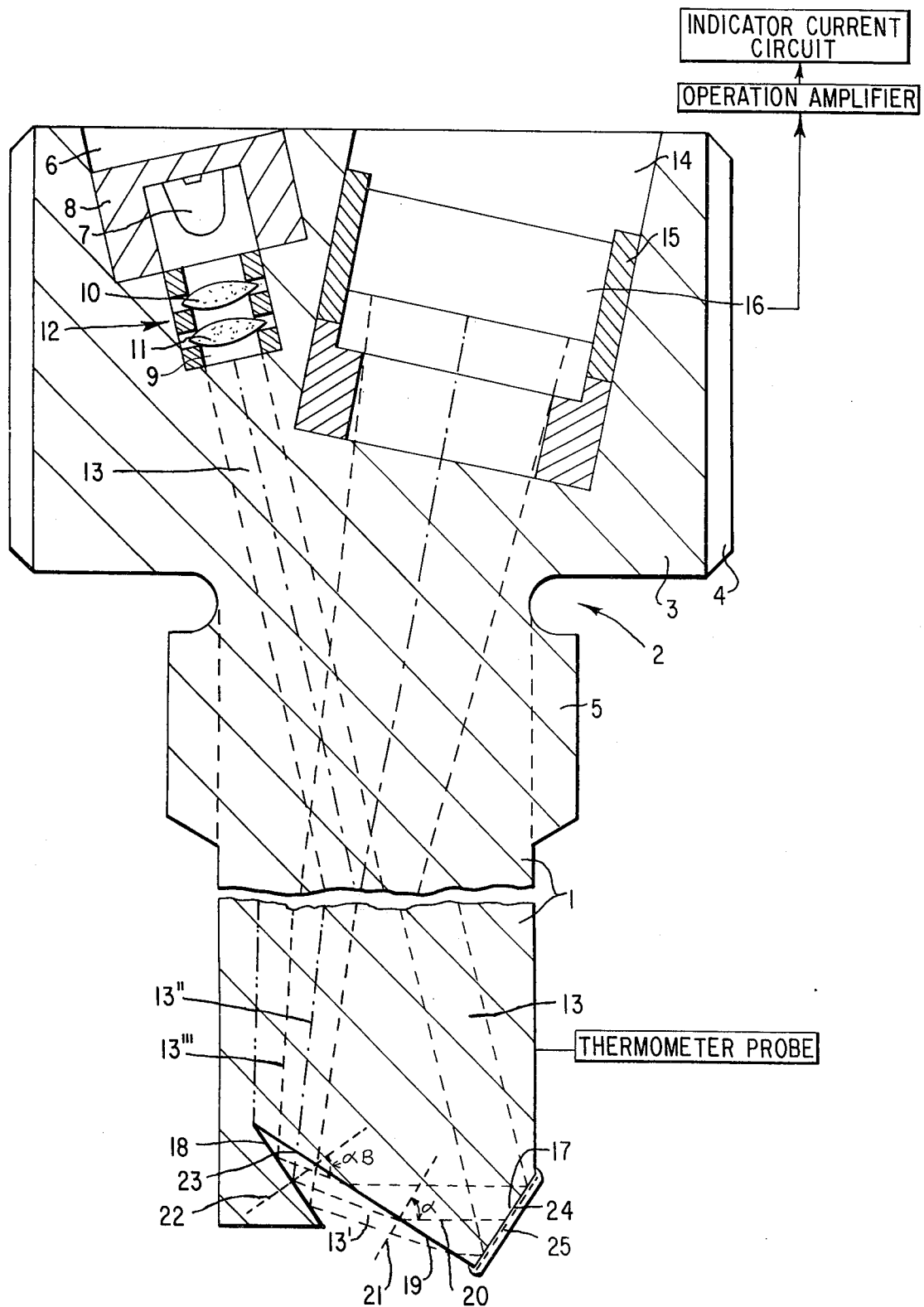

APPARATUS FOR THE CONTINUOUS MEASUREMENT OF THE DENSITY OF A LIQUID BY UTILIZATION OF THE LAW OF REFRACTION

CROSS-REFERENCE TO RELATED APPLICATIONS

Priority of corresponding patent application No. P 23 33 945.9 filed in Germany on July 4, 1973 is claimed under the Convention.

U.S. Pat. applications Nos. 396,560, filed Sept. 12, 1973, for: An Apparatus For Measuring The Density Of A Liquid Utilizing Refraction, and 396,853, filed Sept. 13, 1973, for: An Apparatus For Measuring The Density Of A Contained Liquid By Utilizing The Angular Displacement Of The Limiting Angle At Total Reflection, both of the same co-inventors, and 465,241, filed Apr. 29, 1974, for: Apparatus For Measuring The Density Of A Liquid Utilizing The Law Of Refraction, are made of record, and priorities thereof and of their corresponding German applications Nos. P 22 47 048.0; P 22 47 095.7; P 23 24 259.3. are claimed for all subject matter common with this application.

BACKGROUND OF THE INVENTION

1. Field of the invention

An apparatus for measuring the density of a contained fluid medium by utilizing the angular displacement of the limiting angle of rays with a light transmitting rod.

2. Description of the prior art

The prior art is represented by U.S. Pat. Nos. 2,483,102 to R. M. Pierson of Sept. 27, 1949 for "Refractometer Employing Photosensitive Devices and Use of the Same", and 2,569,127 to G. C. Eltenton of Sept. 25, 1951 for "Refractive Index Measurement of Fluids".

For measuring the density of a liquid, an apparatus with a glass rod immersed in the liquid to be measured is already known. In such a structure, a light source is provided at the end of the glass rod that projects from the liquid, which produces a pencil of light rays which enters parallel to the optical axis of the glass rod. At the end of the immersed glass rod, there are two deflecting surfaces and a measuring surface. The deflecting and measuring surfaces are arranged in such a way that the light pencil passes, by way of one of the deflecting surfaces, at the angle of total reflection, to the measuring surface and therefrom, by way of the other deflecting surface, to an optical system.

Such an apparatus presents the disadvantage that the density of the liquid can be determined only within very narrow limits and subjectively. A continuous measurement of the density by means of this apparatus is therefore not possible.

In another known apparatus, a photoconductive rod is provided. In this structure, at the end of the rod that is immersed in the liquid, a front surface is provided which is perpendicular to the rod axis and which is provided with a reflecting coat. At the rod end that projects from the liquid, a light source and a photosensitive element are provided. In such an apparatus, the light rays entering the photoconductive rod are refracted into the liquid to a greater or smaller extent, depending on the density of the liquid, so that the quantity of light that passes into the liquid is a criterion for the density of the liquid. Such an apparatus makes a continuous measurement possible. However, care must be taken that the depth of immersion of the photoconductive rod always remains the same, since otherwise substantial errors of measurement may result. However, especially in storage batteries, the liquid level varies considerably, so that such an apparatus cannot be used for measuring the acid density of a storage battery.

Another apparatus for measuring the acid density of a storage battery is known, in which a pencil of rays departing from a light source is directed toward several photosensitive receivers through a prism filled with the liquid. Depending on the density of the liquid, the pencil of rays is refracted to a greater or smaller extent by the prism and therefore strikes, according to the index of refraction prevailing in each instance, a photosensitive receiver associated with that index of refraction. Such an apparatus presents the disadvantage that it is of a relatively large structural volume and cannot be installed in the battery casing without extensive alterations thereon. Moreover, this type of an apparatus consists of expensive structural parts and is therefore itself correspondingly expensive.

Finally, an apparatus for measuring the density of a liquid has been proposed which comprises a photoconductive rod with a measuring surface and two reflecting deflecting surfaces at the end of the rod immersed in the liquid, comprising a light source radiating a parallel pencil of rays, and a photosensitive element with a filter wedge arranged in the path of the ray in front of the said photosensitive element. The pencil of rays is directed toward the measuring surface by way of one of the two deflecting surfaces, at an angle with the right angle of the measuring surface, which equals at most the total reflection angle occurring at the lower liquid density limit, and the ray pencil refracted by the surface into the liquid is directed toward a boundary surface of the rod perpendicular to the axis of the ray pencil, behind which boundary surface the other deflecting surface is positioned. By means of such an apparatus it is possible to measure continuously the density of the liquid independently of the liquid level prevailing at each instance. In addition, the structure in comparison with the known devices is cheaper and consists of fewer structural parts, and presents a smaller structural volume so as to be particularly suitable for measuring the acid density of a storage battery.

SUMMARY OF THE INVENTION

The invention aims at making the apparatus last described still less expensive and facilitating the manufacture thereof. This is achieved, according to the invention, by means of an apparatus so arranged that the imaginary plane normal to the deflecting surface, when struck by the refracted pencil of rays, encloses with the pencil of the entering ray the Brewster angle occurring at the greatest density of the liquid.

By this means the pencil of rays reflected by the deflecting surface toward the photosensitive element is completely reflected at the greatest density of the occurring liquid. When the index of refraction of the liquid decreases, which amounts to a decrease in density, the diameter of the reflected pencil of rays diminishes until the pencil of rays finally remains only as a fine line. Such a change in the diameter of the pencil of rays has the effect that, on the one hand, the share of the reflected light decreases, and on the other hand, the light efficiency of the pencil of rays directed toward the photosensitive element increases.

This results in a significantly great change in the electric circuit of the photosensitive element. Due to this control of the photosensitive element, a filter wedge or a polarization filter in the path of the pencil of rays in front of the photosensitive element can be completely dispensed with, which factor affects favorably the cost of manufacture.

A further reduction in the cost of the apparatus of this invention can be achieved by directing the pencil of rays refracted by the measuring surface into the liquid, directly upon the deflecting surface and therefrom, by way of a boundary surface, preferably but not necessarily perpendicular to the axis of the pencil of rays, into the rod upon the photosensitive element. In such a structure of the apparatus a reflecting layer on the deflecting surface becomes superfluous.

The light source advantageously is a gallium arsenide diode with an optical system which is arranged in front of this diode and produces a parallel pencil of rays. By the use of a gallium arsenide diode the structural volume can be kept particularly small. Moreover, a gallium arsenide diode, in contrast to an incandescent lamp operated by means of lowtension voltage, which may also be used, uses less power. The optical system may be constructed of two serially arranged convergent lenses or of one condenser lens molded to the end of the rod that faces the light source.

The photosensitive element employed may be a photoelement, a photodiode, or a photoconductive cell, the latter being particularly advantageous with regard to photosensitivity and cost.

In order to improve the reflection properties, the one should provide a reflecting layer for at least the deflecting surface arranged in the path of the pencil of rays in front of the measuring surface and should cover the reflecting layer with a protective layer. In an apparatus for measuring the acid density of a storage battery, the protective layer applied may, for instance, be bitumen. The reflecting layer may consist of silver, aluminum, or, most advantageously, of gold. In connection with a gallium arsenide diode or with an incandescent lamp operated at low voltage, a gold layer has the advantage that it exhibits an extremely high degree of reflection for the spectrum of the light emanated by such a light source.

In an embodiment preferred for the measurement of acid density in a storage battery, the photoconductive rod is transformed, at its upper end, into a battery closure plug in whose head the light source and the photoconductive element are arranged. Such a structure of the apparatus not only requires no structural changes whatsoever in the battery casing but also requires no additional fastening means for fastening the apparatus to the battery casing. This fact results in the advantage that the apparatus can be assembled to the battery casing by inexperienced personnel and thus also by the motorist himself. The embodiment described is therefore excellently suited for reconditioning of storage batteries already mounted in the motor vehicle.

The photoconductive rod may be fastened to the battery closure plug by means of a screw or plug connection, in which structure, in the case of a screw connection, the rod at the end facing away from the measuring surface may be provided with an external thread, and the closure plug with a corresponding internal thread. A shaping of the photoconductive rod and the battery closure plug as a one-piece unit of plastic material has proved particularly suitable. This results in considerable manufacturing advantages since such a structure can be manufactured in a single operation in an injection molding or pressing process.

As is known, the density of the acid in a storage battery is a function of the temperature, that is to say it decreases when the temperature rises. Since, however, the viscosity of the acid likewise decreases with rising temperature and this effect outweights the other, the acid of the battery yields a greater amount of charge at increasing temperature in spite of decreasing density. According to a further concept of the invention, this dependence can be taken into account by the device of providing, on or in the portion of the photoconductive rod that is immersed in the liquid, a thermometer probe, the output signal of which is fed to the indicating circuit as a corrective value.

The invention will be explained in detail with the aid of the drawing which in a partly diagrammatical illustration contains an embodiment presented by way of example.

BRIEF DESCRIPTION OF THE DRAWING

The sole FIGURE of drawings is a vertical cross-sectional partially diagrammatic view of the apparatus of the invention.

DESCRIPTION OF THE PREFERRED EMBODIMENTS

The apparatus contains a photoconductive rod 1, which at one end is transformed into a portion 2 shaped as a battery closure plug and forms therewith a singlepiece unit of polymethacrylate. The closure plug element comprises a head 3 having a periphery provided with a knurl 4 and a threaded portion 5.

A bore 6 is provided in the closure plug 2 which holds a gallium arsenide diode 7 mounted in a support 8. The support is longitudinally displaceable. A second bore 9 is provided, concentrically to the first bore 6. An optical system 12 consisting of two converging lenses 10 and 11 for producing a pencil of parallel light rays 13 is mounted in the second bore. In a third bore 14 is positioned a photoconductive cell 16 serving as photosensitive element and connected directly or indirectly, by way of an operation amplifier to an indicator current circuit of the measuring apparatus, which is mounted in the socket 15.

At the free end of the photoconductive rod are provided two deflecting surfaces 17 and 18, deflecting surface 17 being positioned in the path of the pencil of rays in front of the measuring surface 19. The deflecting surface 17 reflects the pencil of rays 13 toward the measuring surface 19 so that the pencil of rays with its longitudinal axis 20 strikes the measuring surface at an angle $\alpha$ with respect to the normal to the measuring surface, which angle equals the total reflection angle occurring at the lower acid density limit. For a motor vehicle starter battery designed for Central Europe, the lower acid density limit is approximately 1.18 kg/l. It occurs in a discharged lead storage battery. To this value corresponds an index of refraction of the acid of about 1.3642, so that, at an index of refraction of the photoconductive rod of polymethylmethacrylate of about 1.49, the total reflection angle is approximately 65°.

The other deflecting surface 18 is positioned in the path of light rays behind measuring surface 19 and is struck by a pencil of rays 13' refracted by measuring surface 19 into the acid. The deflecting surface 18 is inclined with respect to the pencil of rays 13' in such a manner that its imaginary normal plane 22 encloses with the entering pencil of rays 13' the Brewster angle ($\alpha$B) which results at the greatest acid density. In the present case, the upper acid density limit prevailing in a charged lead storage battery amounts to about 1.28 kg/l. The index of refraction that corresponds to this value is 1.380. Therefrom and from the index of refraction of the conductive rod of polymethylmethacrylate, a Brewster angle of 47.2 degrees of angle can be calculated. All aforementioned density values apply at a temperature of 27°C.

A pencil of rays 13'' reflected by the deflecting surface 18, at the greatest acid density, toward the approximately perpendicular boundary surface 23 and the photoconductive cell 16 arranged behind the boundary surface 23 is completely reflected at surface 18. When the acid density decreases, the diameter of the pencil of rays 13'' also decreases. When the lower limit of acid density is reached, the pencil of rays has degenerated to a fine line 13'''. The fraction of light refracted at the deflecting surface 18 into the photoconductive rod does not affect the measurement.

What is claimed is:

1. Apparatus for the continuous measurement of the density of a liquid within prespecified limits by utilization of the law of refraction, particularly for the continuous measurement of the acid density of a storage battery of a motor vehicle for the purpose of determining the state of charge of the battery, comprising:

an elongated light-transducing rod mounted for immersion into the liquid;

a measuring surface located at the immersion end of said rod;

a light source mounted to emit a pencil of rays which is at least nearly parallel into said rod toward said measuring surface;

said measuring surface being positioned on said rod to direct said pencil of rays at an angle taken with respect to a normal to the said measuring surface that equals at most the total reflection angle occurring at the lower density limit of said liquid;

a deflecting surface 18 arranged in the path of said pencil of rays for deflecting rays refracted into the liquid by the measuring surface;

a photosensitive element located in the path of said pencil of rays refracted by the said measuring surface into the said liquid and subsequently deflected by the deflecting surface;

a plane (22) normal to the said deflecting surface being positioned to enclose with the said pencil or rays the Brewster angle ($\alpha$B) occurring at the greatest density of the liquid.

2. An apparatus for the continuous measurements of the density of a liquid as claimed in claim 1, further comprising:

a boundary surface mounted at an angle to the axis of the said pencil of rays;

said rod, said measuring surface and the said deflecting surface located relative said boundary surface to direct said pencil of rays refracted by the said measuring surface into the said liquid to pass directly toward the said deflecting surface and therefrom by way of the said boundary surface into the said rod toward the said photosensitive element.

3. An apparatus for the continuous measurements of the density of a liquid as claimed in claim 1, said light source comprising a gallium arsenide diode with an optical system arranged in front of the said diode to produce a parallel pencil of rays.

4. An apparatus for the continuous measurements of the density of a liquid as claimed in claim 1, said photosensitive element being a photoconductive cell.

5. An apparatus for the continuous measurements of the density of a storage battery as claimed in claim 1, said photoconductive cell being shaped at its upper end into a battery closure plug, said light source and the said photosensitive element being provided in the head of said rod.

6. An apparatus for the continuous measurements of the density of a storage battery as claimed in claim 5, said battery closure plug forming with the said photoconductive cell a one-piece integral unit of plastic material.

7. An apparatus for the continuous measurements of the density of a liquid as claimed in claim 1, further comprising a thermometer probe connected with the portion of the photoconductive cell immersed in the liquid.

8. An apparatus for the continuous measurements of the density of a liquid as claimed in claim 1, at least the said deflecting surface arranged in the path of the said pencil of rays in front of the said measuring surface being provided with a reflecting layer and the said reflecting layer being covered with a protective layer.

9. An apparatus for the continuous measurements of the density of a liquid as claimed in claim 8, said reflecting layer consisting of gold.

* * * * *